(12) United States Patent
Yang et al.

(10) Patent No.: US 9,078,848 B2
(45) Date of Patent: Jul. 14, 2015

(54) BIOLOGICAL METHOD TO REDUCE WETWOOD CONTENT IN GREEN LUMBER

(75) Inventors: Dian-Qing Yang, Quebec (CA); Marc Savard, Quebec (CA)

(73) Assignee: FPINNOVATIONS, Pointe-Claire, QC (CA)

( * ) Notice: Subject to any disclaimer, the term of this patent is extended or adjusted under 35 U.S.C. 154(b) by 59 days.

(21) Appl. No.: 13/813,274

(22) PCT Filed: Jul. 27, 2011

(86) PCT No.: PCT/CA2011/000874
§ 371 (c)(1),
(2), (4) Date: Mar. 25, 2013

(87) PCT Pub. No.: WO2012/016326
PCT Pub. Date: Feb. 9, 2012

(65) Prior Publication Data
US 2014/0205850 A1 Jul. 24, 2014

Related U.S. Application Data

(60) Provisional application No. 61/344,493, filed on Aug. 6, 2010.

(51) Int. Cl.
| | | |
|---|---|---|
| *B27K 3/00* | (2006.01) | |
| *A61K 36/06* | (2006.01) | |
| *C12N 1/14* | (2006.01) | |
| *F26B 5/00* | (2006.01) | |
| *F26B 1/00* | (2006.01) | |

(52) U.S. Cl.
CPC ............... *A61K 36/06* (2013.01); *B27K 3/002* (2013.01); *C12N 1/14* (2013.01); *F26B 1/00* (2013.01); *F26B 5/00* (2013.01); *F26B 2210/16* (2013.01); *Y10T 428/662* (2015.04)

(58) Field of Classification Search
USPC ................................. 428/537.1, 384
IPC .................... B27K 5/00,3/00, 3/34; B05D 1/18, B05D 3/00; A01N 59/00, 63/00, 63/04
See application file for complete search history.

(56) References Cited

U.S. PATENT DOCUMENTS

| | | | |
|---|---|---|---|
| 6,475,566 B1 * | 11/2002 | Messner et al. ............... | 427/325 |
| 2006/0246570 A1 * | 11/2006 | Farrell et al. .................. | 435/278 |

FOREIGN PATENT DOCUMENTS

| | | | |
|---|---|---|---|
| CA | 2274481 | * | 11/1999 |
| CA | 2274481 C | | 5/2003 |
| WO | 9915321 | | 4/1999 |

OTHER PUBLICATIONS

Bauch et al., "Biolological Investigations for the Improvement of the Permeability of Softwoods", Holzforschung (1970), 24(6), pp. 199-205.
Lihra, T. 1999. Détermination de la perméabilité du bois de sapin baumier affecté par les poches humides. M.Sc. thesis, Faculté de Foresterie et de Géomatique, Univesité Laval, Québec, Canada.
Lihra, T. 1999. Détermination de la perméabilité du bois de sapin baumier affecté par les poches humides. M.Sc. thesis, Faculté de Foresterie et de Géomatique, Université Laval, Québec, Canada (English translation).
Linares-Hernandez, A. and E.M. Wengert. 1997. End coating logs to prevent stain and checking. Forest Products Journal 47 (4):65-70.
Schink, B., J.C. Ward and J.G. Zeikus. 1981a. Microbiology of wetwood: importance of pectin degradation and *Clostridium* species in living trees. Applied and Environmental Microbiology 42(3):526-532.
Schink, B., J.C. Ward and J.G. Zeikus. 1981b. Microbiology of wetwood: role of anaerobic bacterial populations in living trees. Journal of General Microbiology 123:313-322.
Schneider, M.H. and L. Zhou. 1989. Characterization of wetwood from four balsam fir trees. Wood and Fiber Science 21(1) 1-16.
Verkasalo, E., R.J. Ross, A.TenWolde and R.L. Youngs. 1993. Properties related to drying defects in red oak wetwood. Forest Products Laboratory Research Paper FPL-RP-516, US (pp. 1-10).
Yang, D.-Q., 2009, Biological treatment to improve wood product quality and durability—Fifteen years of effort and experience at FPInnovations—Forintek Division. Paper presented in 40th IRG Annual Meeting on May 24-28, 2009, Beijing, China. Doc. No. IRG/WP09-40444 (pp. 1-10).
Yang, D.-Q., 2008, Reduction of wetwood content in lumber by biological treatment. In: Proceedings of Quality Drying for the 21st Century: Energy and Market Realities. Forest Products Society, Madison, WI, USA, pp. 99-106.
Behrendt et al., "Biological processing of pine logs for pulp and paper production with *Phlebiopsis gigantea*", Journal of Applied and Environmental Microbiology, May 1997, pp. 1995-2000 abstract; p. 1999.
Notification of First Office Action, China, CN 201180045096.8, Sep. 2, 2014.

* cited by examiner

*Primary Examiner* — Leszek Kiliman
(74) *Attorney, Agent, or Firm* — Norton Rose Fulbright Canada LLP

(57) ABSTRACT

The present invention relates to a method for reducing wetwood content in green lumber by a treatment with a selected fungal species, such as *Phlebiopsis gigantea* or *Gliocladium roseum*, prior to kiln drying. In the laboratory conditions, the biological treated boards reduced wood moisture content (MC) by 22-37% more than untreated boards. The time required for drying biological treated boards was approximately reduced by 10% compared with untreated controls, and by 33% compared with freshly-saw lumber. After drying, the biological treated boards reduced the total deformation with stain, warping and checking by 14-25%.

9 Claims, 1 Drawing Sheet

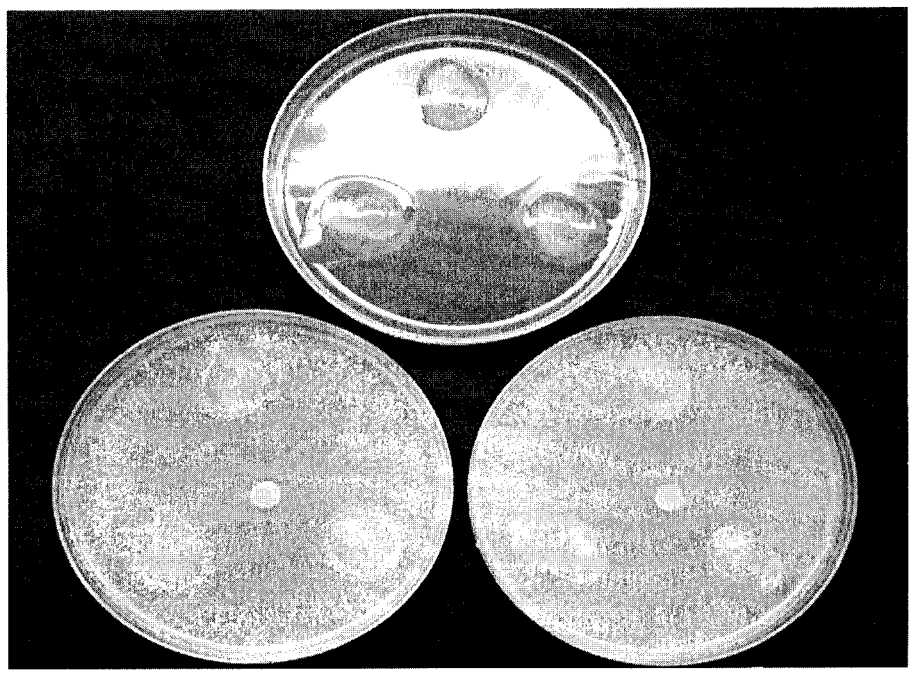

BIOLOGICAL METHOD TO REDUCE WETWOOD CONTENT IN GREEN LUMBER

CROSS-REFERENCE TO RELATED APPLICATIONS

This application is a National entry of PCT/CA2011/000874 filed Jul. 27, 2011, in which the United States of America was designated and elected, and which remains pending in the International phase until Feb. 6, 2013, which application in turn claims priority under 35 USC 119(e) from U.S. Provisional Application Ser. No. 61/344,493, filed Aug. 6, 2010.

TECHNICAL FIELD

This invention relates to a method for reducing wetwood content from green lumber including freshly-sawn lumber with a fungal species, prior to kiln drying.

BACKGROUND ART

Wetwood, or water pocket, has a water-soaked appearance that occurs in the wood of living trees, including many hardwood and softwood species (Libra, 1999). Wetwood is caused by anaerobic bacteria that enter wood through wounds and lesions in trunks and roots of young trees. The affected wood is dead and changes to yellowish green or without any distinctive colour but can be recognized by its sour odour. Compared with normal sapwood, wetwood has less extractible carbohydrate content, such as sugars, but higher level of mineral and organic compounds. The zone of wetwood has a pH of 1-2 units higher than unaffected areas, and contains gas under pressure.

Cellulose, hemicellulose and lignin are the main components of wood cell walls, and the chemical structure and interrelationships of these components in wood cells are well known (Zabel and Morrell 1992). In addition to these main structural compounds, pectin is another polymer commonly located in the middle lamella and primary cell wall of trees, and acts as a cementing substance there (Schink et al. 1981a). Several anaerobic fermentative bacteria produce pectinolytic enzymes that destruct vessel and ray pit membranes of wood (Schink et al. 1981b). The reproduction and metabolites of these bacteria form a foetid liquid in wood, which results in a high moisture content of the wetwood. Since moisture content of wetwood is much higher than the normal wood, it usually requires relatively long periods for adequate drying (Schneider and Zhou 1989). The slow drying of the wetwood pocket compared to the surrounding wood, possibly due to blockage of pathways by bacterial mucilage, creates steep moisture gradients creating greater internal stresses within the lumber. Furthermore, degradation of pectic substances of the middle lamella causes the weakness of chemical bonds between wood cells. Consequently, weak bonding causes a high risk for developing checks, splits, crook, bow and twist of lumber in kiln drying (Ward and Pong 1980, Verkasalo et al. 1993). The lower permeability of wetwood compared to normal wood also affects the wood's treatability with preservatives.

Wetwood causes serious problems for lumber drying and utilization. The economic losses resulting from this defect are enormous. If wetwood problem can be solved, the value of lumber will be increased and the benefit for sawmills will be significant. Based on a conservative estimate, if lumber grade recovery can be increased by 5% and drying times can be reduced by 15% with a defined method (Linares-Hernandez and Wengert 1997), a sawmill producing 100 MMfbm per year with 20% lumber containing wetwood would save over $500,000 per year.

Many studies have been conducted on wetwood using various physical, chemical, or mechanical methods, but the problem has yet to be solved.

DISCLOSURE OF THE INVENTION

This invention seeks to provide a method of reducing wetwood content in green lumber or freshly-sawn lumber.

This invention also seeks to provide a method for producing a dried lumber from a green lumber having a wetwood content.

The invention also seeks to provide a treated green lumber.

Still further the invention seeks to provide a dried green lumber.

In accordance with the invention, there is provided a method of reducing wetwood content in green lumber comprising treating the green lumber with at least one fungal species in water or in an alkaline solution.

In another aspect of the invention, there is provided a method of producing a dried lumber comprising: treating a green lumber having a wetwood content with at least one fungal species in water or in an alkaline solution; allowing the at least one fungal species to reduce the moisture content of the green lumber; and kiln drying the green lumber of reduced moisture content.

The present invention provides an effective method for reducing wetwood content of freshly-sawn lumber or green lumber with a selected fungal species.

The invention also provides the method of producing a treatment solution for wetwood using *P. gigantea* or *G. roseum* as inoculum.

Furthermore, the invention provides a treating process of unseasoned softwood lumbers.

BRIEF DESCRIPTION OF THE DRAWING

FIG. 1 is a photograph illustrating growth of a wetwood causal bacterium (B-a) and a promising fungal candidate (*Phlebiopsis gigantea*) in 2% malt extract agar plates in an antagonistic test (Example 1). The photograph shows the antagonist test with the most promising candidate *Phlebiopsis gigantea* (bottom 2 plates) against wetwood causal agent B-a (upper plate) in agar plates.

DETAILED DESCRIPTION OF THE INVENTION AND PREFERRED EMBODIMENTS

This invention relates to a method which uses a biological agent to treat lumber containing wetwood to reduce water content before kiln drying, and represents a new concept for wetwood drying. Wetwood causal bacteria secrete enzymes to degrade pectic substances into monomers, acetic acid, and fatty acids (Schink et al. 1981a). These substances can be utilised by certain fungal species. Some fungi are also able to produce antibiotics to kill bacteria. Because of the anti-bacterial activities of fungi, the foetid liquid in wood can be utilised, and wood vessels can be cleaned by fungal colonization. Consequently, in accordance with the invention, the permeability of wetwood can be increased, the lumber drying time can be reduced and the lumber quality can be improved.

Suitable fungal species include *Phlebiopsis gigantea* (Fr.) Jülich and *Gliocladium roseum* Bainier; as well as combinations of these.

In a preferred embodiment, the selected fungal species used in this invention are *Phlebiopsis gigantea* (Fr.) Jülich (FTK 897B) isolated from balsam fir logs, and *Gliocladium roseum* Bainier (FTK 321U) isolated from root of carrot (deposited in Forintek Culture Collection of Wood-inhabiting Fungi).

The fungal species may be applied in an aqueous vehicle, typically water or an aqueous alkaline solution. By way of example alkalinity may be obtained by alkali metal hydroxides, carbonates or bicarbonates, for example sodium carbonate or sodium bicarbonate.

The fungal species may be applied by immersing the green lumber in a solution of the fungal species, by spraying the green lumber with the solution or by roller application and the like.

Following treatment, the treated green lumber may suitably be stored preferably under controlled conditions of temperature and humidity while reduction of the water content by the fungal species proceeds. Thereafter the green lumber is suitably kiln dried to further reduce the water content.

The mechanism of this invention is that the fungal species absorbs water from the bacteria-formed wetwood in the green lumber, at the same time the fungal species clears bacteria-blocked wood vessels in the green lumber and makes the wood more permeable for water evaporation. A period of time for lumber storage after the treatment allows the fungal species to penetrate into the wood of the green lumber to absorb water and clear the wood vessels.

While the invention has been particularly described by reference to two fungal species it will be understood that these are merely illustrative and the invention extends to other fungal species which grow or metabolise while absorbing water from bacteria-formed wetwood in the green lumber.

Furthermore, while the invention is exemplified for specific wood species in the Examples below, especially black spruce, jack pine and balsam fir, these are merely illustrative and the invention extends to other softwood and hardwood species which have wetwood problems, for example sub-alpine fir, hemlock, Douglas fir, white pine, red oak and aspen. All these wood species have serious wetwood problems.

EXAMPLES

The following examples describe in detail three major experiments conducted in this invention. Example 1 describes a test on selection of fungal candidates in agar plates; Example 2 describes a laboratory test of the selected wetwood control candidates on lumber; and Example 3 describes a field test of the selected wetwood control candidates.

Example 1

The goal of this example was to identify an antagonistic fungus that can kill causal agents of wetwood and utilize their metabolites to reduce the wetness of infected wood. To realize this goal, various fungi species were used against six wetwood causal agents (WCA): A-a (a bacterium isolated from wetwood of aspen), A-c (a yeast isolated from wetwood of aspen), B-a (a bacterium isolated from wetwood of balsam fir), Y-2 (a yeast isolated from wetwood of balsam fir), SaB-2 (a bacterium isolated from wetwood of sub-alpine fir), and SaY-4 (a mixture of a yeast and a bacterium isolated from wetwood of sub-alpine fir). The tests were conducted in Petri plates containing a 2% malt extract agar medium (MEA). Each bacterium was inoculated at 3 points that were 2 cm away from the edge of the plate. All plates were incubated at 25° C. for 3 days, and then a mycelium plug of the test fungus, either *Phlebiopsis gigantea* or *Gliocladium roseum*, was placed in the center of each plate. Three replicates were used for each combination. The plates were placed back in a growth chamber at 25° C., and the competition reaction between the two micro-organisms was observed at 3, 7, 11, and 15 days.

Results showed that wetwood causal organisms grew well on MEA plates prior to challenge with antagonistic fungi. In the first 3 days, the colonies of the wetwood causal organisms grew 0.9-1.1 cm in diameters (Table 1). After inoculation with the antagonistic fungi, *P. gigantea* or *G. roseum*, the growth of the wetwood causal organisms was much reduced. In most cases, the growth of the wetwood causal organisms were completely stopped and were overcome by the antagonistic fungi in 11 days (FIG. 1).

Example 2

This example examined the efficacy of the treatments of wetwood lumber with selected wetwood control candidates in the laboratory conditions. The selected fungal species, *Phlebiopsis gigantea* and *Gliocladium roseum*, were cultured in 1-L flasks containing 500 ml of 1.5% malt extract broth medium. The flasks were incubated on a shaker (120 rpm) at 25° C. for 14 days, then, mycelia mass inside the flask was ground into a fungal suspension with a homogenizer. The fungal suspension was adjusted to $1 \times 10^6$ segments/ml. A total of 120 boards of black spruce, jack pine and balsam fir (SPF, mostly balsam fir, 2×4 inch×2 feet,) with heavy wetwood were labelled and weighed individually and put in 3 groups, 40 boards each. Two groups of boards were treated with the 2 fungi (each group was treated with 1 fungus); dipping boards 1 minute in a fungal suspension. The solution pick-up was measured as 1400 ml/40 boards. After treatment, 20 boards in each test group were wrapped with a plastic sheet on its 4 sides without stickers between boards. Two bundles of boards in the same treatment group were piled together with stickers between bundles in an environmentally controlled chamber at 20° C. and 70% RH. One group of untreated boards was put in the same way as treated boards and served as controls. The boards were inspected after 8 weeks in storage. The evaluation and measurements included: 1) evaluate the growth of molds, stain and decay on each board; 2) weigh each board; 3) seal ends of boards with a colorless wax; 4) load boards in a kiln; 5) run kiln; 6) weigh some movable samples from each treatment group at 7, 23, 30, 48, 72 and 96 hrs to determine wood moisture content (MC) of samples during drying; 7) after most boards were dried to around 10% MC, stop the kiln drying; 8) weigh each board again; 9) evaluate deformation (splits, checks, crook, bow, and twist) appeared in each board; and 10) cut some boards from each test group (cut 2 wood blocks from each board), oven drying and determine MC of wood blocks. The program of the kiln drying schedule is described in Table 2.

After an 8-week storage period in the laboratory conditions (20° C. and 70% RH), untreated boards had an average MC of 101.7% (Table 3), and 2 groups of biological treated boards lost more MC, compared with the untreated boards. The boards treated with *P. gigantea* had a MC of 69.5%, whereas those treated with *G. roseum* had an MC of 79.5%. The 22-32% MC differences between biological treated and untreated boards are considered to be the reduction of wetwood contents in boards caused by the treatment. During kiln drying, the MCs of bio-treated and untreated boards were continually decreased with increasing drying time. After 96 hours in the drying process, the MCs of *P. gigantea* and *G.*

*roseum* treated boards were 8.8% and 9.7%, respectively, whereas MC of untreated boards was 15%. To further dry untreated boards to the same level of MC as the bio-treated boards (such as for remanufacturing), an increase of drying time by 10% (10.5 hours) would be required. Conversely, if the treated lumber were to be simply used for framing with a target average MC of 16%, a shorter drying time could be used.

After the storage, all untreated boards (100%) were fully covered by molds and stain, which is usually considered as unacceptable for use (Table 4). Molds and stain also affected some of the biological treated boards, but the severity of the infection was lighter. *P. gigantea* treated boards had a stain rate of 25%, and *G. roseum* treated boards had a stain rate of 38%. This suggests that not just any naturally occurring mold or stain fungus is capable of eliminating wet pockets and that this capacity may be limited to certain fungi including the two tested here.

After drying, 55% of untreated boards had crook, bow and twist, and 38% had splits and checks (Table 4). The total rate of sound boards without any deformation in the untreated group was 0%. Compared with untreated controls, the biological treated boards reduced wood stain by 62-75% and warping by 5-20%, but increased checking by 10-12% caused by lower MC in these boards. This would likely have been less of an issue if the drying time had been shorter and the final moisture content had been around 16%. The total sound boards without any deformation were 24% and 23%, respectively, in the two biologically treated groups.

Example 3

A field trial was performed on 600 SPF boards (mostly balsam fir, freshly-sawn, 2×4 inch×2 feet,) with heavy wetwood in FPInnovations-Forintek Laboratory at Quebec. The boards were divided into 6 groups, each contained 100 boards. Four groups of boards were treated with: 1) *Gliocladium roseum* water suspension; 2) *Phlebiopsis gigantea* water suspension; 3) *G. roseum+P. gigantea* (1:1) water suspension; and 4) *G. roseum+P. gigantea* (1:1) in 4% sodium carbonate and 1% sodium bicarbonate solution. Boards were dipped 1 minute in a fungal suspension. The solution pick-up was measured as 274 mL/m$^2$ of board surface area. One group of boards served as untreated controls and another group was stored at −20° C. as fresh controls. After treatment, boards in each test group were piled in two bundles; each contained 50 boards and with stickers between each layer of boards. Two bundles of boards in each treatment group were piled together in a Forintek's yard and loosely covered with a plastic sheet over the top of each pile to prevent direct rain penetration. There was natural air circulation between boards. After 8 weeks of outdoor storage, treated and untreated boards, as well as fresh controls were evaluated, measured and dried in the same way as those boards in the laboratory test described in Example 2. The kiln drying schedule for this batch of boards was the same as the one described in Table 2.

Fresh boards had an initial average MC of 125% (Table 5, at 0 hour before kiln drying). After an 8-week storage period in the field conditions, air-dried untreated boards had an average MC of 41% (Table 5, at 0 hour). All biological treated boards, except for those treated with *G. roseum* alone, had similar MCs after the storage, between 47-56%. The boards treated with *G. roseum* alone had the highest MC (70%) after the field storage. During kiln drying, the MCs of all boards continually decreased as the drying time increased (Table 5). After 90 hours of the drying process, the MCs of biological treated and untreated boards were reduced to a similar level, between 10-13%, whereas fresh boards were still at 27% MC. To further dry fresh boards to the same level of MC as the bio-treated boards, an increase of drying time by 33% (48 hours) would be required.

Under field conditions, after 8 weeks in storage, 75% of untreated boards were heavily affected by molds and stain at a level rated unacceptable (Table 6). The best treatment was with the combination of *G. roseum* and *P. gigantea* in an alkaline solution; all boards treated with this solution were clear or with only a trace of mold/stain infection. The second most effective treatment was with the combination of *P. gigantea* and *G. roseum* in water, which had 14% of boards affected. The stain infection of *P. gigantea* treated boards was 22%, whereas stain on *G. roseum* treated boards was 42%.

After kiln drying, untreated boards had the highest rates of warping (52%) and checking (63%), and only 5% of boards were sound without any deformation (Table 6). Compared with untreated controls, the biological treated boards reduced wood stain by 33-75%, warping by 2-13% and checking by 3-30%. The total defects were reduced by 14-25%, depending on the treatments. Fresh (frozen) boards also had lower percentages of deformation but that was due to their not being fully dried. In the laboratory conditions, the biological treated boards reduced wood moisture content (MC) by 22-37% more than untreated boards. The time required for drying biological treated boards was approximately reduced by 10% compared with untreated controls, and by 33% compared with freshly-saw lumber. After drying, the biological treated boards reduced the total deformation with stain, warping and checking by 14-25%.

TABLE 1

Growth of wetwood causal organisms on agar plates challenged with the two most effective fungal species

| Fungus vs. wetwood causal organisms | Growth of wetwood causal organisms (cm in diameter) | | | |
|---|---|---|---|---|
| | 3 days | 7 days | 11 days | 14 days |
| *Gliocladium roseum* vs. Say-4 | 0.9 | 0.3 | 0.0 | 0.0 |
| *Gliocladium roseum* vs. Y-2 | 1.0 | 0.6 | 0.2 | 0.1 |
| *Gliocladium roseum* vs. A-a | 1.0 | 0.6 | 0.2 | 0.1 |
| *Gliocladium roseum* vs. A-c | 0.9 | 0.2 | 0.1 | 0.0 |
| *Gliocladium roseum* vs. B-a | 1.0 | 0.5 | 0.1 | 0.1 |
| *Gliocladium roseum* vs. Sab-2 | 1.0 | 0.3 | 0.1 | 0.0 |
| *Phlebiopsis gigantea* vs. Say-4 | 0.9 | 0.2 | 0.0 | 0.0 |
| *Phlebiopsis gigantea* vs. Y-2 | 1.1 | 0.6 | 0.0 | 0.0 |
| *Phlebiopsis gigantea* vs. A-a | 1.1 | 0.7 | 0.0 | 0.0 |
| *Phlebiopsis gigantea* vs. A-c | 1.0 | 0.4 | 0.0 | 0.0 |
| *Phlebiopsis gigantea* vs. B-a | 0.9 | 0.7 | 0.0 | 0.0 |
| *Phlebiopsis gigantea* vs. Sab-2 | 1.1 | 0.4 | 0.0 | 0.0 |

TABLE 2

Kiln drying schedule for bio-treated and untreated wetwood lumber

| Stage | Time (h) | Db temperature (° C.) | Wb temperature (° C.) |
|---|---|---|---|
| Pre-heating | 4 | 74 | 68 |
| Equilibrate | 2 | 74 | 68 |
| >30% TH | | 77 | 68 |
| 30-25% TH | | 79 | 63 |
| 25-20% TH | | 82 | 60 |
| <20% TH | | 82 | 54 |

TABLE 3

Moisture content (MC) of boards at different kiln drying times in the laboratory test

| Treatment | MC (%) at different hours of kiln drying | | | | | | |
|---|---|---|---|---|---|---|---|
| | 0 | 7 | 23 | 30 | 48 | 72 | 96 |
| Gliocladium roseum | 79.5 | 76.5 | 53.5 | 47.0 | 35.1 | 25.2 | 9.7 |
| Phlebiopsis gigantea | 69.5 | 65.5 | 46.1 | 40.4 | 30.3 | 22.9 | 8.8 |
| Untreated control | 101.7 | 97.7 | 67.6 | 58.6 | 43.3 | 30.5 | 15.0 |

TABLE 4

Defect development on boards after kiln dry in the laboratory test

| Treatment | Staining %* | Warping % | Checking % | Sound % |
|---|---|---|---|---|
| Gliocladium roseum | 38 | 35 | 50 | 24 |
| Phlebiopsis gigantea | 25 | 40 | 48 | 23 |
| Untreated control | 100 | 55 | 38 | 0 |

*Percent rated unacceptable

TABLE 5

Moisture content (MC) of boards at different times of kiln drying in the field test

| Treatment | MC (%) at different hours of kiln drying | | | | |
|---|---|---|---|---|---|
| | 0 | 22 | 46 | 70 | 90 |
| Gliocladium roseum | 69.9 | 49.5 | 32.6 | 19.4 | 12.4 |
| Phlebiopsis gigantea | 46.9 | 34.0 | 24.8 | 15.6 | 9.8 |
| Gliocladium roseum + Phlebiopsis gigantea | 52.8 | 41.3 | 30.9 | 20.4 | 12.8 |
| Gliocladium roseum + Phlebiopsis gigantea + alkaline | 56.4 | 44.9 | 34.5 | 23.1 | 11.6 |
| Untreated control | 40.5 | 31.9 | 25.1 | 18.4 | 9.6 |
| Fresh | 124.9 | 97.7 | 70.2 | 41.2 | 27.0 |

TABLE 6

Defect development on boards after kiln dry in the field test

| Treatment | Staining %* | Warping % | Checking % | Sound % |
|---|---|---|---|---|
| Gliocladium roseum | 42 | 39 | 33 | 24 |
| Phlebiopsis gigantea | 22 | 50 | 60 | 19 |
| Gliocladium roseum + Phlebiopsis gigantea | 14 | 39 | 55 | 26 |
| Gliocladium roseum + Phlebiopsis gigantea + alkaline | 0 | 50 | 40 | 30 |
| Untreated control | 75 | 52 | 63 | 5 |
| Fresh | 0 | 39 | 56 | 25 |

*Percent rated unacceptable

REFERENCES

Lihra, T. 1999. Détermination de la perméabilité du bois de sapin baumier affecté par les poches humides. M. Sc. thesis, Faculté de Foresterie et de Géomatique, Université Laval, Québec, Canada.

Linares-Hernandez, A. and E. M. Wengert. 1997. End coating logs to prevent stain and checking. *Forest Products Journal* 47 (4):65-70.

Schink, B., J. C. Ward and J. G. Zeikus. 1981a Microbiology of wetwood: importance of pectin degradation and *Clostridium* species in living trees. *Applied and Environmental Microbiology* 42(3):526-532.

Schink, B., J. C. Ward and J. G. Zeikus. 1981b. Microbiology of wetwood: role of anaerobic bacterial populations in living trees. *Journal of General Microbiology* 123:313-322.

Schneider, M. H. and L. Zhou. 1989. Characterization of wetwood from four balsam fir trees. *Wood and Fiber Science* 21(1) 1-16.

Verkasalo, E., R. J. Ross, A. TenWolde and R. L. Youngs. 1993. Properties related to drying defects in red oak wetwood. Forest Products Laboratory Research Paper FPL-RP-516, US.

The invention claimed is:

1. A method of reducing wetwood content in green lumber comprising treating the green lumber with *Phlebiopsis gigantea* (Fr.) Jülich in water or in an alkaline solution.

2. The method according to claim 1, wherein said *Phlebiopsis gigantea* (Fr.) Jülich is in water.

3. The method according to claim 1, wherein green lumber is sawn green lumber of softwood.

4. The method according to claim 3, wherein said softwood is balsam fir, jack pine or black spruce.

5. The method according to claim 1, wherein said green lumber is dipped in a solution of said *Phlebiopsis gigantea* (Fr.) Jülich in said water or alkaline solution.

6. The method according to claim 1, wherein said treating is followed by storage of the treated green lumber while *Phlebiopsis gigantea* (Fr.) Jülich reduces the water content of the green lumber.

7. The method according to claim 1, wherein said green lumber is balsam fir, jack pine, black spruce sub-alpine fir, hemlock, Douglas fir, white pine, red oak or aspen.

8. A method of producing a dried lumber comprising:
   treating a green lumber having a wetwood content with *Phlebiopsis gigantea* (Fr.) Jülich in water or in an alkaline solution;
   allowing the *Phlebiopsis gigantea* (Fr.) Jülich to reduce the moisture content of the green lumber; and
   kiln drying the green lumber of reduced moisture content.

9. A dried green lumber produced according to claim 8.

\* \* \* \* \*